United States Patent
Byrd et al.

(12) 
(10) Patent No.: US 6,203,590 B1
(45) Date of Patent: Mar. 20, 2001

(54) SURGICAL SMOKE EVACUATION SYSTEM WITH REPLACEABLE FILTER CARTRIDGE MODULE AND ACCUMULATED FILTER USAGE DISPLAY

(76) Inventors: Robert J. Byrd, 111 Ashley Dr., Marbury, AL (US) 36051; Jay S. Northington, 1664 London Towne La., Montgomery, AL (US) 36117; Roland D. Block, 1461 White Ash Dr., Painesville, OH (US) 44077; Roger G. Ignon, 843 Ave. C, Redondo Beach, CA (US) 90277; Alejandro Herrera, 840 Mandevilla Way, Corona, CA (US) 91719

(*) Notice: Subject to any disclaimer, the term of this patent is extended or adjusted under 35 U.S.C. 154(b) by 0 days.

(21) Appl. No.: 09/275,710

(22) Filed: Mar. 25, 1999

(51) Int. Cl.[7] .................. B01D 29/56; B01D 35/143; B01D 50/00; A61B 19/00
(52) U.S. Cl. .................. 55/319; 55/385.2; 55/467; 55/485; 55/486; 55/503; 55/507; 96/416; 96/448; 96/422; 96/424; 604/319
(58) Field of Search .................. 55/385.1, 385.2, 55/467, 473, 485, 486, 507, 505, 319, 503; 604/319, 322, 902, 35; 96/417, 422, 416, 424, FOR 167, 418

(56) References Cited

U.S. PATENT DOCUMENTS

| | | |
|---|---|---|
| 3,923,482 | 12/1975 | Knab et al. . |
| 4,468,217 | 8/1984 | Kuzmick et al. . |
| 4,619,672 | 10/1986 | Robertson . |
| 4,642,128 * | 2/1987 | Solorzano ............... 55/467 |
| 4,796,795 | 1/1989 | Urban . |
| 4,810,269 | 3/1989 | Stackhouse et al. . |
| 4,905,578 | 3/1990 | Curtis et al. . |
| 4,963,134 * | 10/1990 | Backscheider et al. ............... 55/467 |
| 4,986,839 * | 1/1991 | Wertz et al. ............... 55/467 |
| 5,039,316 * | 8/1991 | Hunter et al. ............... 55/385.2 |
| 5,047,072 | 9/1991 | Wertz et al. . |
| 5,226,939 * | 7/1993 | Nicolas et al. ............... 55/467 |
| 5,242,474 * | 9/1993 | Herbst et al. ............... 55/467 |

(List continued on next page.)

FOREIGN PATENT DOCUMENTS

| | | |
|---|---|---|
| 41 21 069 | 2/1992 | (DE) . |
| 2 046 858 | 11/1979 | (GB) . |

OTHER PUBLICATIONS

"Surgical Smoke Evacuation System", *Health Devices*, vol. 26, No. 4, Apr. 1997, pp. 131–176.
K.A. Ball, "Controlling Smoke Evacuation and Odor During Laser Surgery", *Today's OR Nurse*, vol. 8, No. 12, Dec. 1986, pp. 5–10.
Stackhouse "Laser Smoke Filtration System."
Stackhouse Systems—One page description—undated.

*Primary Examiner*—David A. Simmons
*Assistant Examiner*—Robert A. Hopkins

(57) ABSTRACT

An evacuation system is provided for removing smoke generated during a surgical procedure performed in a surgical room. The evacuation system includes a pre-filter assembly and a replaceable filter cartridge module disposed in the surgical room to permit replacement of used filter cartridge modules with new filter cartridge modules by personnel within the surgical room. A vacuum generator is disposed outside of the surgical room and includes a vacuum pump for establishing an air flow through the replaceable filter cartridge module. The pre-filter assembly includes an elongate flexible suction hose that is adapted for manipulation into position adjacent the medical procedure. A mechanical connection mechanism enables pre-filter assemblies to be easily replaced between each surgical procedure. An accumulated filter usage circuit calculates a quantity of filter capacity available and generates a filter loading signal based on the available capacity. The filter usage is calculated by adjusting usage counter in proportion to the speed of a vacuum motor and pump mechanism.

21 Claims, 6 Drawing Sheets

U.S. PATENT DOCUMENTS

| | | | |
|---|---|---|---|
| 5,264,026 | * 11/1993 | Paul | 55/467 |
| 5,281,246 | 1/1994 | Ray et al. . | |
| 5,336,128 | 8/1994 | Birdsong . | |
| 5,427,569 | 6/1995 | Plymoth . | |
| 5,531,802 | * 7/1996 | Schlor et al. | 55/467 |
| 5,578,000 | 11/1996 | Greff et al. . | |
| 5,636,627 | 6/1997 | Rochester . | |
| 6,045,596 | * 4/2000 | Howland, Jr. et al. | 55/385.2 |

* cited by examiner

SURGICAL SMOKE EVACUATION SYSTEM WITH REPLACEABLE FILTER CARTRIDGE MODULE AND ACCUMULATED FILTER USAGE DISPLAY

BACKGROUND OF THE INVENTION

The subject invention is directed toward the art of medical equipment and, more particularly, to a surgical smoke evacuation system with a unitary filter cartridge module that can be easily replaced and further, including filter usage circuit and display device that accurately shows actual filter usage and is easily readable by medical equipment operators.

The invention is especially well suited for incorporation into overhead surgical equipment management systems and will be described with particular reference thereto. However, as will become apparent, the invention is capable of broader application beyond surgical use and could be supported by and/or integrated into a variety of medical equipment apparatus such as, for example, surgical carts and free standing support stands, and further, could be integrated directly into medical operating room walls, ceilings, or floors, or the like.

It is well known that in many forms of laser surgery, orthopedic surgery, and electro-cauterization, smoke is generated including very fine particles of vaporized tissue, blood, and other bodily fluids sometimes mixed with liquids, bone fragments, and other larger sized debris. It is advantageous to the surgeon to not only remove these surgical by-products from the surgical site because they interfere with access to the surgical site, but also to rid the operating room of the by-products so that they are not inhaled or leaked into inappropriate areas. To that end, various tubular fluid suction apparatus have been proposed for removing liquids and large pieces such as bone fragments that are generated and accumulate within the surgical incision. In addition, a wide range of smoke evacuation systems have been proposed for removing finer airborne particles including smoke and other smaller debris that rises from the surgical site and into the air space of the operating room.

One such laser plume evacuation system is described in U.S. Pat. No. 5,409,511 to Paul. As taught there, an elongate section of tubing is carried from the surgical site to a vacuum source by an articulating arm assembly connected from overhead to the ceiling of the operating room. The Paul system proposes a single centrally located centrifugal separator tank, garbage pump, vacuum producer or fan, and HEPA filter, collectively "vacuum source". The vacuum source is sufficiently large to provide adequate air flow to enable multiple simultaneous surgeries to be performed in multiple independent surgical rooms. In that regard, the vacuum source is typically centrally located wherein each of the operating rooms is connected to the vacuum source by a system of tubing strings that are routed overhead through the surgical ceiling network.

One disadvantage of laser plume evacuation systems of the type described is that the filters are not easily replaceable by operating room personnel. The filters are neither modular nor are they located within the same room in which the surgical procedures are performed. Normally, the filters can only be serviced by trained technicians. This makes filter replacement difficult and expensive.

Another disadvantage of the prior art plume evacuation systems is that they offer a mostly inadequate representation of usable filter life remaining. This can compromise surgical procedures because of an inability to properly gauge the useful time remaining on any given filter at the vacuum source. Further, inadequate air flow can unknowingly result when the filter becomes clogged because of gage accuracy limitations.

Typically, filter status signals used in prior art plume evacuation systems are based on calculations derived from either a pressure differential signal or a strict timer value. Commonly, a pressure transducer is disposed adjacent or across the filter medium in order to sense a pressure differential developed between air flows upstream and downstream from the filter medium. As the filter becomes worn and clogged, the pressure differential developed across the filter increases. For that reason, pressure differential type systems are usually accurate only when used within a narrow range of air flow rates. Simple system changes, such as replacing a suction hose with another having a different length or diameter, can result in completely inaccurate pressure differential readings.

Alternatively, absolute counters or timers have been proposed to essentially log total filter usage. The counter or timer is reset whenever the filters are replaced. However, much of the usable filter life is usually wasted because the timers are typically set to expire prematurely based on a "worst case" usage estimate. The counters are almost completely inaccurate when the vacuum system is used outside of its normal flow rate range of operation and when system parameters are changed such as with hose replacement as noted above.

It would therefore be desirable to provide a surgical smoke evacuation system that enables easy filter replacement by personnel in the operating room.

It would also be desirable to provide a replaceable pre-filter assembly including an elongate suction hose segment and a pre-filter housing for collecting larger airborne particles and that is replaceable for each surgical procedure. In that way, a single main smoke filter cartridge module could be used for multiple surgical procedures by simply replacing the pre-filter assembly between each use.

It would further be desirable to provide a means for generating an accurate accumulated filter usage signal that could be used by operating room personnel during surgical procedures to quickly and easily ascertain the usable filter life remaining. Preferably, the accumulated filter usage signal would be an enhanced hybrid of the above-noted strict timer based and strict pressure differential based systems so that none of the usable filter life is wasted and to enable the system to be used over a wide range of vacuum air flow rates without erroneous filter life readings.

SUMMARY OF THE INVENTION

The subject invention provides an improvement to the prior art surgical plume evacuation systems of the type described and includes a replaceable filter cartridge module disposed in the operating room to permit replacement of used filter cartridge modules with new filter cartridge modules quickly and easily by personnel located within the operating room. In addition, the invention provides an improved surgical smoke evacuation system that includes a control unit having an accumulated filter usage circuit for calculating a quantity of filter capacity available or remaining in the filter cartridge module based upon accumulated actual drive motor and vacuum source usage. Accumulated filter usage is calculated based on a substantially linear relationship between flow rate and usage time.

In accordance with the subject invention, there is provided an evacuation system for removing smoke generated during a medical procedure performed in an associated medical room. The evacuation system includes a single use (single procedure) pre-filter assembly located in the medical room, a multiple use (multiple procedure) replaceable filter cartridge module also located in the medical room, and a vacuum generator disposed outside of the associated medical room, preferably in the ceiling.

The pre-filter assembly includes a pre-filter housing and an elongate flexible suction hose member having a distal end adapted for manipulation into position adjacent the medical procedure. The flexible suction hose also has a proximal end connected with the pre-filter housing. The replaceable filter cartridge module is adapted to permit replacement of used filter cartridge modules with new filter cartridge modules by personnel within the medical room. The filter cartridge module holds at least one filter element and has an input opening on an input end adapted for selective connection with the pre-filter assembly. Further, the filter cartridge module includes an exhaust opening, the input and exhaust openings defining an internal passageway for communicating an air flow from the input opening and flexible suction hose member to the exhaust opening of the filter cartridge module through the at least one filter element. The vacuum generator is preferably disposed in the medical room ceiling and includes a vacuum source and an elongate tube for establishing fluid communication between the exhaust opening of the filter cartridge module and the vacuum pump. The vacuum source selectively generates the air flow through the elongate tube, the internal passageway, and the pre-filter assembly to remove smoke from the medical procedure. In its preferred form, the vacuum source is comprised of a cooperating vacuum motor and vacuum fan. However, a vacuum pump could be used as well.

In accordance with a further aspect of the invention, the pre-filter assembly includes a pre-filter medium held within the pre-filter housing, the medium having a relatively coarse matt for trapping larger solid particles within the pre-filter housing while permitting smaller particles and smoke to pass therethrough.

Further, although its primary function is to filter particles, in its preferred form, the pre-filter housing is shaped to trap fluids such as blood and the like that is inadvertently collected and entrained in the flow of air passing through the pre-filter housing. This prevents fluids from entering into the filter cartridge module. Still further, the pre-filter housing includes a transparent viewing window to permit the pre-filter media to be viewed without opening the pre-filter housing. In that way, operating room personnel can readily visually ascertain the remaining useful life of the pre-filter medium and capacity of the housing.

In accordance with yet another aspect of the invention, the subject surgical smoke evacuation system includes a control unit having at least one manually operable mode control switch disposed in the surgical room for use by personnel during surgical procedures. The control unit is in operative control of the vacuum source to selectively cause the vacuum motor and fan or vacuum pump to generate the air flow through the elongate tube, the internal passageway, and the pre-filter assembly to remove airborne particles and smoke from the medical procedure based on a position of the manually operable mode control switch.

Still yet further, the control unit includes an air flow rate or volume control switch disposed in the medical room. The control unit is in operative control of the vacuum source to selectively cause the vacuum motor and fan to generate the vacuum air flow over a range of flow rates, preferably a continuous range, based on a position of the manually operable volume control switch. Alternatively, the vacuum source could be operated over a set of predefined discrete flow rates selected within the full air flow rate range.

In its preferred form, the control unit includes an accumulated filter usage circuit for calculating a quantity of filter capacity available in the filter element contained within the replaceable filter cartridge module. Still further, the control unit includes a filter loading display device located in the surgical room to provide visual indicia of the quantity of filter capacity available to personnel located within the medical room.

In accordance with yet a further aspect of the invention, the accumulated filter usage circuit determines the quantity of filter capacity available by adjusting a usage counter in proportion to at least one of the continuous range of flow rates or series of staggered discrete flow rates as determined by the motor and vacuum pump and the position of the manually operable volume control switch. In that way, filter usage is calculated based on a relationship, preferably linear, between flow rate and usage time.

Still yet further in accordance with another aspect of the invention, a pivotable door member is provided at the input opening of the replaceable filter cartridge module. The door member includes a curved lead edge portion adapted to engage a corresponding lip formed on the pre-filter housing. In its preferred form, the door member is biased into a closed position by a spring. When the door is closed, it blocks the input opening into the filter cartridge module to prevent ingress of contaminants and the like. During use of the subject surgical system, the lead edge of the door member is held in an engaged position with the corresponding lip formed on the pre-filter housing to hold the housing in place on the face of the cartridge module during surgical procedures.

It is a primary object of the invention to provide a surgical smoke evacuation system that includes a replaceable filter cartridge module located within the medical room to permit easy replacement of used filter cartridge modules with new filter cartridge modules by personnel in the surgical room. Preferably, each replaceable filter cartridge module is usable in multiple surgical procedures.

A further object of the invention is the provision of a replaceable pre-filter assembly including a pre-filter housing holding a pre-filter medium for trapping solid particles within the pre-filter housing while permitting smoke to pass therethrough. Preferably, the housing body is shaped to trap fluids that may be inadvertently collected within the lower portion of the housing and includes an opaque portion to enable the pre-filter media to be viewed without opening the pre-filter housing.

Yet another object of the invention is the provision of an accumulated filter usage signal and display for use by surgical room personnel to easily determine the remaining useful life of the replaceable filter cartridge module.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
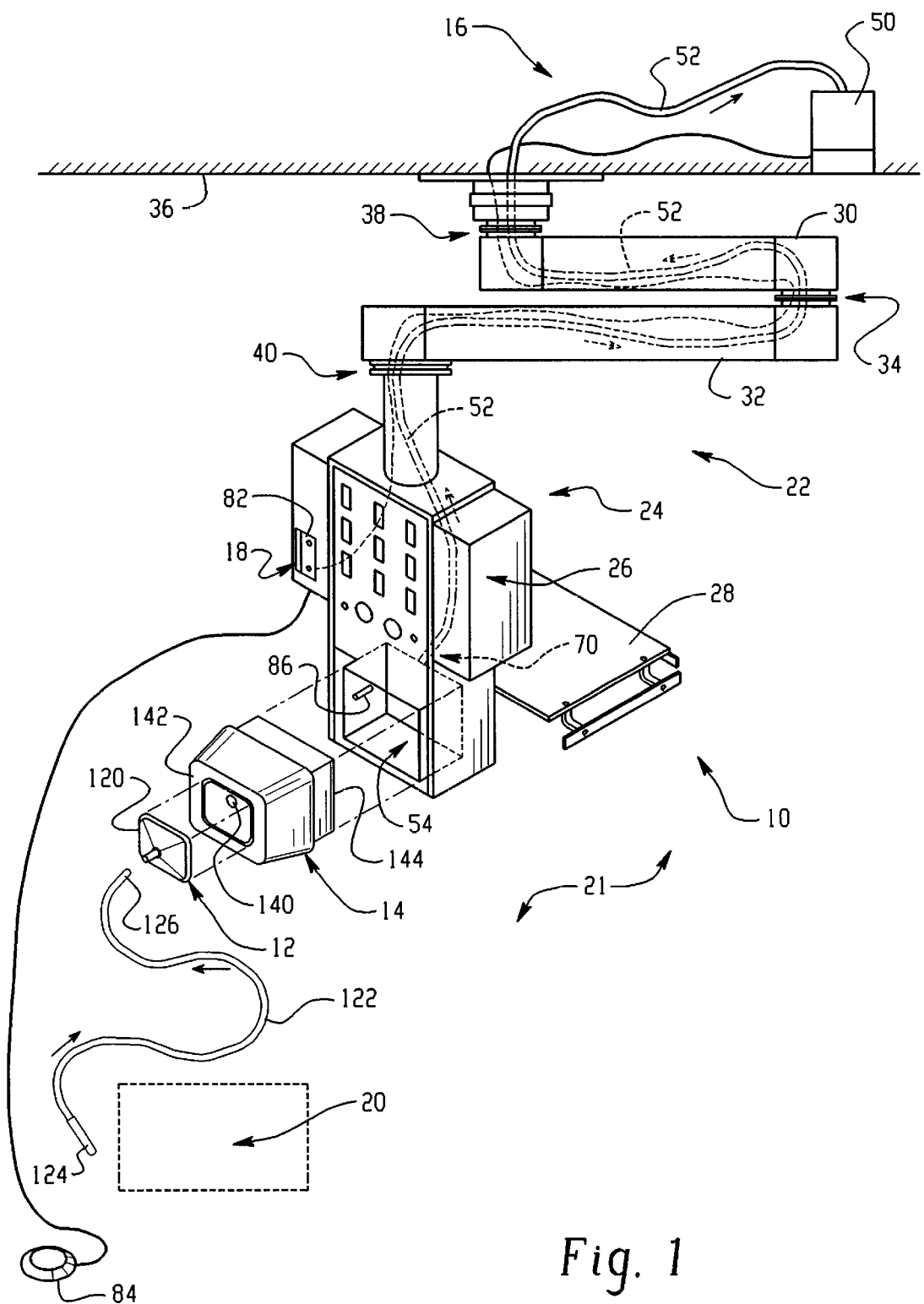
FIG. 1 is a somewhat diagrammatic pictorial view showing the overall arrangement of the surgical smoke evacuation system formed in accordance with the preferred embodiment of the invention and integrated into an associated overhead medical equipment support apparatus.

Referring now to the drawings wherein the showings are for the purposes of illustrating the preferred embodiment of the invention only and not for purposes of limiting same, FIG. 1 illustrates the overall arrangement of a surgical smoke evacuation system 10 formed in accordance with the present invention for removing smoke, contaminants, and other airborne debris that are generated as by-products of certain surgical procedures. In its preferred form, the subject smoke evacuation system 10 includes a pre-filter assembly 12 that is selectively connected to a replaceable filter cartridge module 14 which is in turn connected to a vacuum generator 16. A control unit 18 is in operative control over the vacuum generator 16 to selectively cause the vacuum generator to initiate a suction-type airflow through the pre-filter assembly 12 and the filter cartridge module 14 so that smoke, contaminants, and other airborne debris can be efficiently and easily removed from an associated surgical site 20.

Although the subject system can be held in place relative to the surgical site 10 by any appropriate means such as by use of any generic medical equipment support apparatus 22, a dedicated cart system (not shown), or the like, it is preferred that the smoke evacuation system 10 is integrated into an overhead medical equipment support appliance 24 as shown so that the system is easy to use. Generally, the support appliance 24 includes a main body column 26 that is adapted to support a horizontally extending main platform 28 for holding medical devices, test equipment, and other items in position adjacent the surgical site 20.

As shown, the support appliance 24 includes upper and lower support arm members 30, 32 that are preferably rotatably connected at a pivot joint 34. Each of the upper and lower support arm members are in turn respectively pivotally connected to the ceiling 36 and main body column 26 by suitable rotatable joints 38 and 40. As can be seen, the overhead medical equipment support appliance 24 is readily positioned into place adjacent a surgical site 20 by merely manually orienting the main body column 26 and platform 28 into the desired position and then moving the column on the arm members into the desired location.

The support appliance 24 provides a convenient vehicle for positioning the disposable or "renewable" portions of the subject system at readily accessible locations. To that end, it is of particular importance to one aspect of the present invention that the filter cartridge module 14 is disposed in the surgical room 21 adjacent the surgical site 20 so that used filter cartridge modules can be replaced with new filter cartridge modules easily and conveniently by personnel within the surgical room 21. As will be described below, the replaceable filter cartridge modules 14 are usable for multiple surgical procedures. Each pre-filter assembly 12, however, is usable for only a single surgical procedure. Replacement of the non-reusable or single use pre-filter assembly 12 after each procedure is made easy in accordance with the present invention by providing a mechanical connection interface that is simple to use for connecting the pre-filter assembly into operative position on the filter cartridge module.

Figure 2:
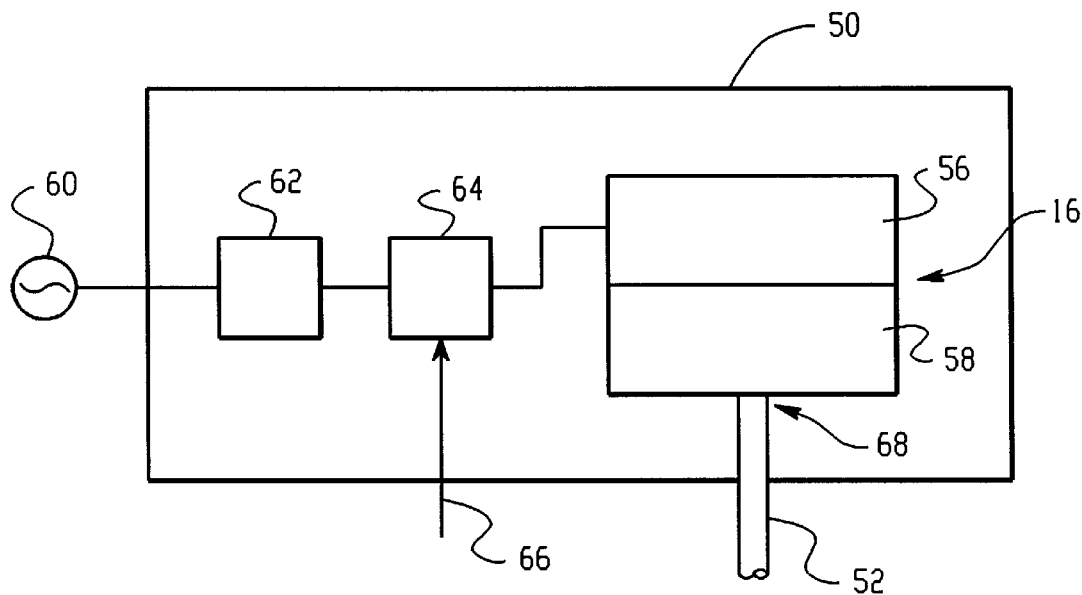
FIG. 2 is a diagrammatic pictorial view showing the overall arrangement of the evaluation module portion of the smoke evacuation system illustrated in FIG. 1.

As shown generally in FIG. 1 and to some extent to a greater degree in FIG. 2, the vacuum generator 16 includes an evaluation module 50 located in the ceiling 36, an elongate section tube 52 carried within the support arm members 30, 32, and a box shaped plenum 54. The evaluation module 50 essentially includes a variable speed vacuum motor 56 that is preferably directly connected to a vacuum fan or pump device 58. The vacuum motor 56 is connected to an associated source of power 60 through a circuit breaker bank 62 and a speed control and power conversion circuit 64. Preferably, the speed control circuit includes a set of solid state circuit elements, such as SCRs and TRIACs for interfacing the variable speed vacuum motor 56 to the power source 60 based on speed command signals carried on a command signal line 66. The speed control circuit 64 uses well known phase control techniques to gate the TRIACs into conduction over a range of conduction angles relative to the power source frequency so that the speed of the vacuum motor 56 is regulated in accordance with the speed command signal on the signal line 66.

As shown in the figures, the elongate suction tube 52 has a proximal end 68 connected to the vacuum pump 58 and a distal end 70 connected to the box-shaped plenum 54. In that way, the reduced pressure generated by the variable speed vacuum motor and fan is communicated through the suction tube 52 to the plenum 54. Preferably, the suction tube 52 is flexible so that the upper and lower support arm members 30, 32 together with the main body column 26 can be oriented into multiple positions adjacent the surgical site 20 without kinking the tube.

Figure 3:
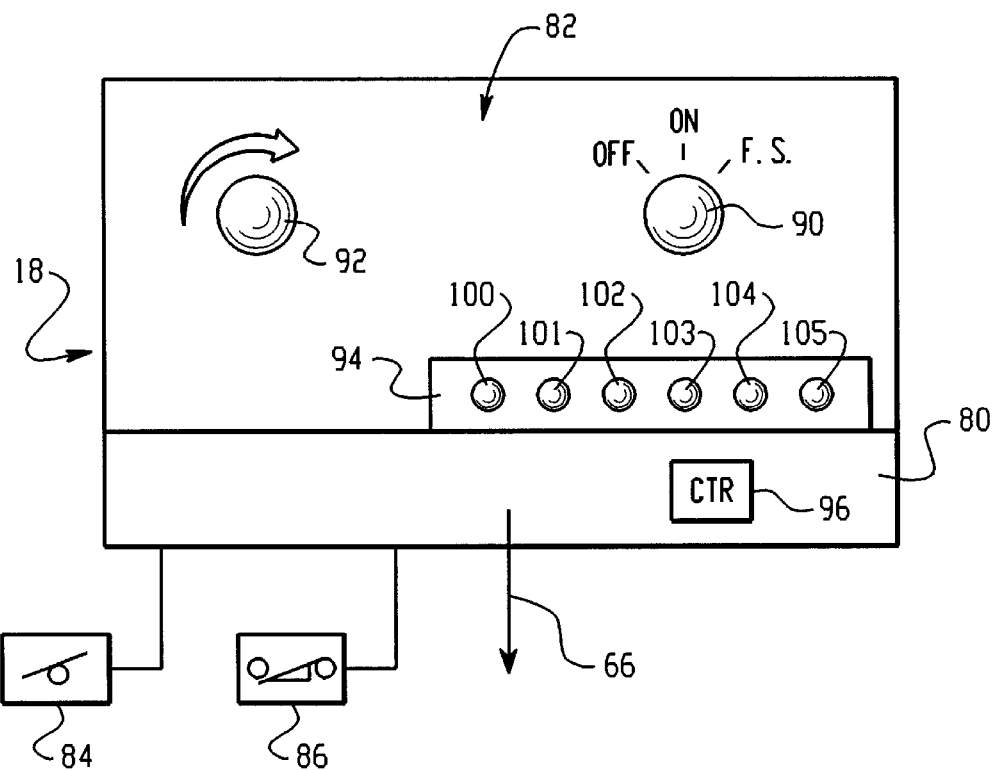
FIG. 3 is a diagrammatic pictorial view showing the overall arrangement of the control module portion of the surgical smoke evacuation system illustrated in FIG. 1.

With yet continued reference to FIG. 1 and with additional reference to FIG. 3, the control unit 18 includes a control module 80 disposed within the main body column 26 of the associated medical equipment support appliance 24. In addition, the control unit includes a control panel 82 located on a face of the main body column 26 as shown and a foot switch 84 disposed in a convenient location on the floor of the surgical room 21. Further, the control unit 18 includes a filter cartridge module present sensor 86 for generating a signal when the filter cartridge module 14 is received in the box-shaped plenum 54.

As will be described in greater detail below, the control module 80 preferably includes a digital computer with a processor for generating a signal indicative of the amount of usable filter life remaining. The module present sensor 86 is used for resetting a counter when an old filter cartridge module is replaced with a new filter cartridge module. The digital computer of the control module includes non-volatile memory for storing the count value so that the count is not lost or re-set when power is removed from the system.

As best shown in detail in FIG. 3, the control panel 82 includes a mode control switch 90, a vacuum volume control switch 92, and a filter accumulated usage meter 94. Preferably, in accordance with the present invention, all of the above operator interfaces are arranged on the control panel in the operating room for convenient and unobtrusive operator access.

Turning first to the mode control switch 90, it can be seen that the subject surgical smoke evacuation system 10 includes an "ON" mode, an "OFF" mode and a "FOOT-SWITCH" mode. Obviously, in the OFF mode, the control module 80 generates no speed control signal on the command signal line 66 so that the variable speed vacuum motor 56 remains motionless and in that way generates no vacuum. When the mode control switch 90 is placed into the ON position, the control module 80 generates an appropriate command signal level on the command signal line 66 commensurate with a position of the vacuum volume control switch 92 so that the speed control circuit 64 regulates the speed of the variable speed vacuum motor 56 to produce a vacuum-type air flow in the elongate suction tube 52. More particularly, when the mode control switch 90 is in the ON position, the position of the vacuum volume control switch 92 is used by the control module to selectively cause the vacuum fan 58, through the speed control circuit 64, to generate a vacuum-type air flow in the elongate suction tube 52 over a continuous range of flow rates based on the position of the manually operable vacuum volume control switch 92. Alternatively, as described above the volume control switch could be used to activate the vacuum source at a plurality of predefined settings to establish a corresponding set of discrete vacuum flow rates over the range of flow rate capability of the vacuum source.

The FOOTSWITCH position of the mode control switch 90 is interpreted by the control module 80 to cause the variable speed vacuum motor 56 to operate at the variable speed dictated by the volume control switch 92, but only when the FOOTSWITCH 84 is depressed by an operator in the surgical room 21. In that way, the FOOTSWITCH can be used by surgical room personnel to activate and deactivate the subject surgical smoke evacuation system 10 in a "hands free" manner. After the vacuum flow rate is selected through adjustment of the vacuum volume control switch 92, the FOOTSWITCH is usable to selectively activate and deactivate the smoke evacuation system without further adjustment.

Table I below summarizes the operational modes of the subject surgical smoke evacuation system 10 for the various positions of the mode control switch 90.

TABLE I

| MODE CONTROL SWITCH (90) POSITION | MOTOR FUNCTION (56) | TIME LEFT LED (94) |
|---|---|---|
| "OFF" Position | OFF | OFF |
| "ON" Position (Foot switch has no effect) | | |
| Filter Installed | RUNNING | ON |
| Filter Removed | OFF | ON |

TABLE I-continued

| MODE CONTROL SWITCH (90) POSITION | MOTOR FUNCTION (56) | TIME LEFT LED (94) |
|---|---|---|
| "FOOT SWITCH" Position | | |
| Filter Installed ON Foot Sw ON | RUNNING | ON |
| Filter Installed ON Foot Sw OFF | OFF | ON |
| Filter Removed and Foot Sw ON | OFF | OFF |
| Filter Removed and Foot Sw OFF | OFF | OFF |

Lastly in connection with the control unit portion of the subject smoke evacuation system, a filter accumulated usage meter 94 is provided on the control panel 82 in a manner as shown. Preferably, in accordance with the preferred embodiment of the invention, the filter accumulated usage meter includes a linear arrangement of light emitting diodes (LEDs) 100–105. The LEDs are sequentially staged, one after the other, in a bar graph style to provide a visual indication to operating room personnel of the amount of usable filter cartridge module life remaining. Preferably, the right most LED 105 is amber, the next right most LED 104 is amber, and the remaining LEDs 100–103 are green in color.

Of particular importance to another aspect of the present invention, the LEDs 100–105 are sequentially illuminated in accordance with a unique filter usage calculation algorithm executed by the control module 80. Unlike strict time based counters that are used in some prior art systems, an internal counter mechanism 96 of the subject smoke evacuation system is sequenced at varying rates dependent upon the speed at which the variable speed vacuum motor 56 is driven. Accordingly, the internal filter cartridge module counter is pulsed at a rate that is proportional to a position of the vacuum volume control switch 92 and, accordingly, is also proportional to the rate of air flow through the suction tube 52 and the filter cartridge module 14. The control module determines the quantity of filter capacity available in the filter cartridge module 14 by adjusting a frequency of the usage counter 96 in proportion to the range of vacuum flow rates generated by the variable speed vacuum source. The LEDs 100–105 are selectively illuminated when the counter reaches predetermined threshold values. Preferably, the threshold values are programmable so that they can be changed by authorized personnel, as necessary, to adapt the system to accommodate physical changes that affect flow rate such as, for example, hoses of different length or inner diameter, and the like.

The preferred algorithm executed by the control module 80 for sequentially illuminating the filter loading signal 96 by sequentially illuminating the LEDs 100–105 to present a visual display of usable filter life remaining is shown in Table II below. By way of example only, when the vacuum volume control switch 92 remains in the 0–10 percent mode, the second LED 101 is illuminated after 6 hours of system operation, the third LED is illuminated after 12 hours, the fourth LED after 18 hours, the fifth LED after 24 hours, and, lastly, the amber LED 105 is illuminated after 30 hours of smoke evacuation system operation. Essentially, when plotted, each of the operational ranges versus filter use indicias defines a slope. The slope of each curve represents the frequency of adjusting the usage counter in proportion to the position of the volume control switch and the speed of the vacuum motor. As the speed of the motor is increased or decreased, the counter frequency is adjusted accordingly.

TABLE II

| SPEED CONTROL POSITION | LED 2 | LED 3 | LED 4 | LED 5 | LED 6 |
|---|---|---|---|---|---|
| 0 TO 10%-NORMAL MODE | 6 HRS | 12 HRS | 18 HRS | 24 HRS | 30 HRS |
| 10 TO 20%-NORMAL MODE | 6.4 HRS | 12.8 HRS | 19.2 HRS | 25.6 HRS | 32 HRS |
| 20 TO 30%-NORMAL MODE | 6.8 HRS | 13.6 HRS | 20.4 HRS | 27.2 HRS | 34 HRS |
| 30 TO 40%-NORMAL MODE | 7.2 HRS | 14.4 HRS | 21.6 HRS | 28.8 HRS | 36 HRS |
| 40 TO 50%-NORMAL MODE | 7.6 HRS | 15.2 HRS | 22.8 HRS | 30.4 HRS | 38 HRS |
| 50 TO 60%-NORMAL | 8 HRS | 16 HRS | 24 HRS | 32 HRS | 40 HRS |
| 60 TO 70%-NORMAL MODE | 8.4 HRS | 16.8 HRS | 25.2 HRS | 33.6 HRS | 42 HRS |
| 70 TO 80%-NORMAL MODE | 8.8 HRS | 17.6 HRS | 26.4 HRS | 35.2 HRS | 44 HRS |
| 80 TO 90%-NORMAL MODE | 9.2 HRS | 18.4 HRS | 27.6 HRS | 36.8 HRS | 46 HRS |
| 90 TO 100%-NORMAL MODE | 9.6 HRS | 19.2 HRS | 28.8 HRS | 38.4 HRS | 48 HRS |

In the preferred embodiment, the filter usage calculation is based primarily on carbon filter usage to control odors. When odors are not an issue or when a carbon filter is not employed, the linear relationships set out in the table above is adjusted accordingly.

Figure 4:
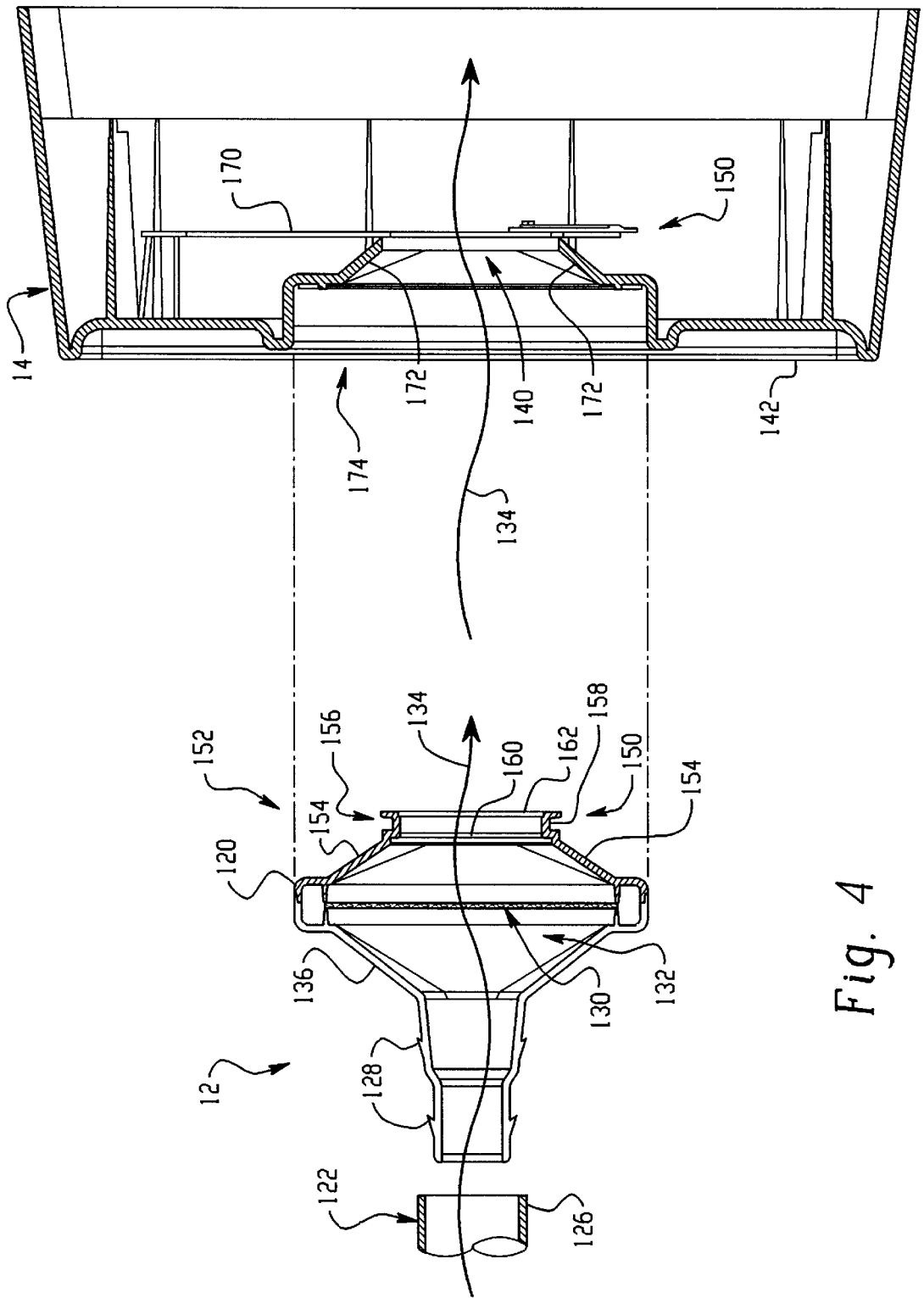
FIG. 4 is a cross-sectional view of the pre-filter assembly and replaceable filter cartridge module portions of the subject smoke evacuation system taken on line 4—4 of FIG. 1.

With attention now to FIGS. 1 and 4, it is seen that the pre-filter assembly 12 includes a pre-filter housing 120 and an elongate flexible suction hose 122 having a distal end 124 adapted for manipulation into position adjacent the surgical site 20 and a proximal end 126 connected to the pre-filter housing 120. In use, the suction hose 122 operates as a type of wand that can be grasped by the hand, bent as desired, and oriented in suitable positions to draw smoke, airborne contaminants, and other debris away from the surgical site. Preferably, the proximal end 126 is fastened to the housing 120 using a set of tubing barbs 128. The barbs ensure that once installed, the suction hose is difficult to remove from the housing.

As best shown in FIG. 4, the pre-filter assembly 12 includes a pre-filter medium 130 held within the housing 120. Preferably, the pre-filter medium 130 has a relatively coarse mat for trapping solid particles within the housing while permitting smoke to pass therethrough. In addition, as shown in cross section in FIG. 4, the pre-filter housing 120 is shaped to have a larger central region 132 whereat the traveling air flow tends to reduce in speed to enable heavier particles and fluids that may be collected incidentally, to precipitate therefrom and accumulate in the lower portion of the housing. In that way, the pre-filter housing 120 is shaped to trap heavier and larger sized particles entrained in the flow of air 134 passing through the pre-filter housing and pre-filter medium. A transparent viewing window 136 is formed on the top side of the pre-filter housing 120 to enable the pre-filter medium 130 to be viewed without opening the pre-filter housing itself. The pre-filter housing can be easily adapted for use with a fluid canister device to provide fluid collection capability to the subject system. As an example, a tube could be provided between an opening in the lower housing area and a fluid collection canister.

As shown best in FIG. 1, the replaceable filter cartridge module 14 has an input opening 140 on an input end thereof 142 and an exhaust opening (not shown) on an exhaust end 144 thereof. In that way, an air flow is communicated from the input opening 140 through the cartridge module 14 toward the exhaust end and into the box-shaped plenum 54 of the vacuum generator 16. At least one ultra low penetration air filter (not shown) and at least one charcoal filter (not shown) is incorporated into the filter cartridge module.

As noted above, it is an advantage of the present invention that the pre-filter assembly is disposable after each use (single procedure use). In that regard, in order to make attachment and detachment of the pre-filter assembly relative to the filter cartridge module easy, a mechanical connection mechanism 150 is provided.

Turning first to FIG. 4, the pre-filter housing 120 is formed on one end to define a tapered region 152 having a series of angled flat surfaces 154 formed around an annular grooved nose portion 156. As shown, a circular retaining groove 158 is formed between a pair of circular shoulders 160, 162. The retaining groove 158 is adapted to receive the curved edge of a shutter-type pivot door 170 carried on the filter cartridge module 14. Also, the series of angled flat surfaces 154 are arranged and positioned on the pre-filter housing 120 to conform to the size and shape of a corresponding set of angled flat surfaces 172 formed on the input end 142 of the filter cartridge module 14.

Figure 5:
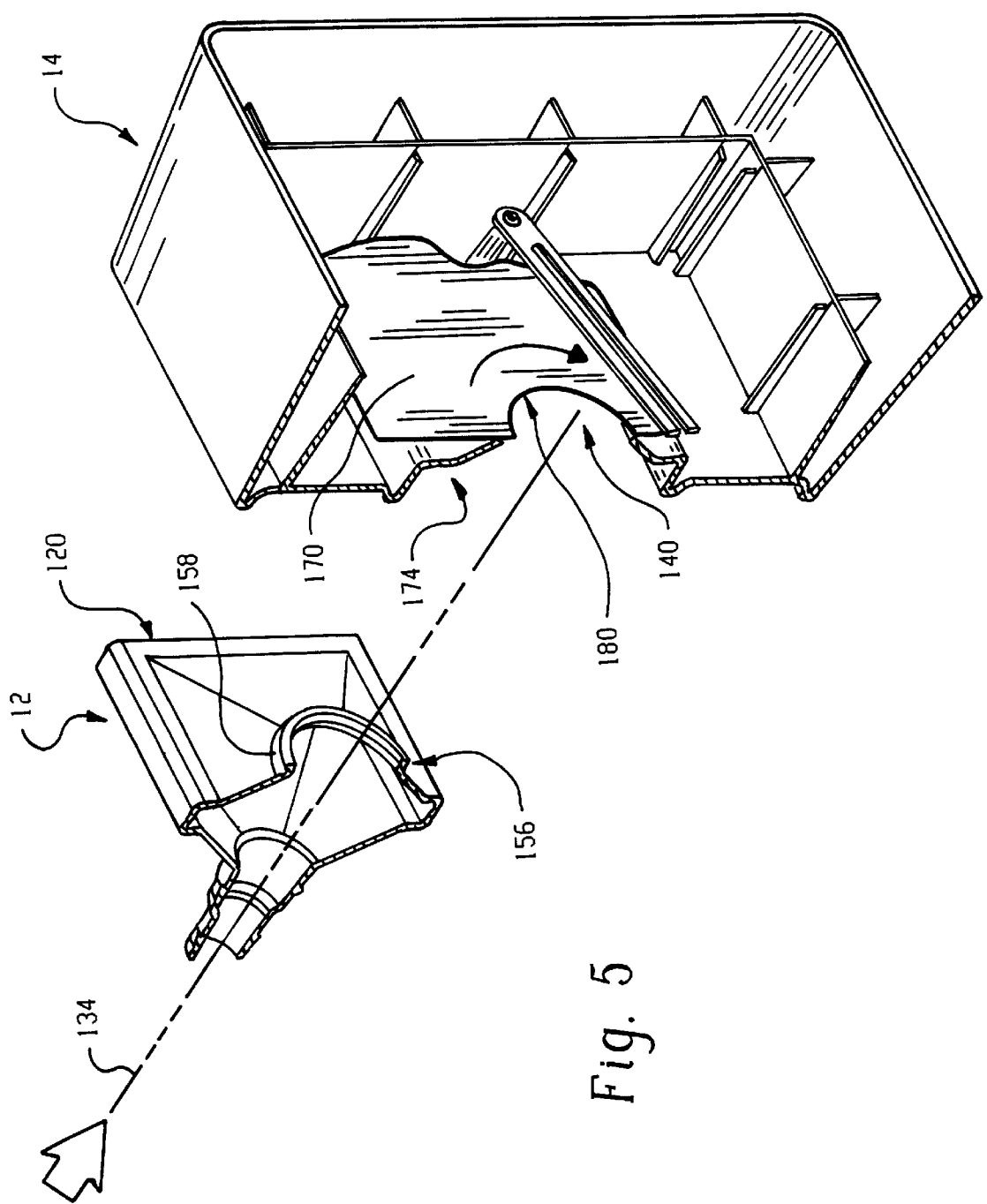
FIG. 5 is an exploded isometric view in partial cut-away of the pre-filter assembly and filter cartridge module portions illustrated in FIG. 4 shown in their respective aligned pre-connected orientations.

As shown best in FIG. 5, the pre-filter housing 120 is substantially rectangular in shape and, accordingly, is adapted to be snugly received into a correspondingly shaped pocket region 174 defined in the input end 142 of the filter cartridge module. Those skilled in the art will appreciate that the housing and pocket region can take on any shape including round or curved configurations, or the like. Further as shown in FIG. 5, the pivot door 170 includes a curved engagement edge 180 that is sized and shaped to be embedded within the retaining groove 158 formed on the nose portion 156 of the pre-filter housing 120. As can be seen, when the pivot door 170 is disposed in a closed position, it operates to close the input opening 140 formed in the filter cartridge module 14. In that way, the filters contained within the module are substantially prevented from becoming contaminated.

Figure 6:
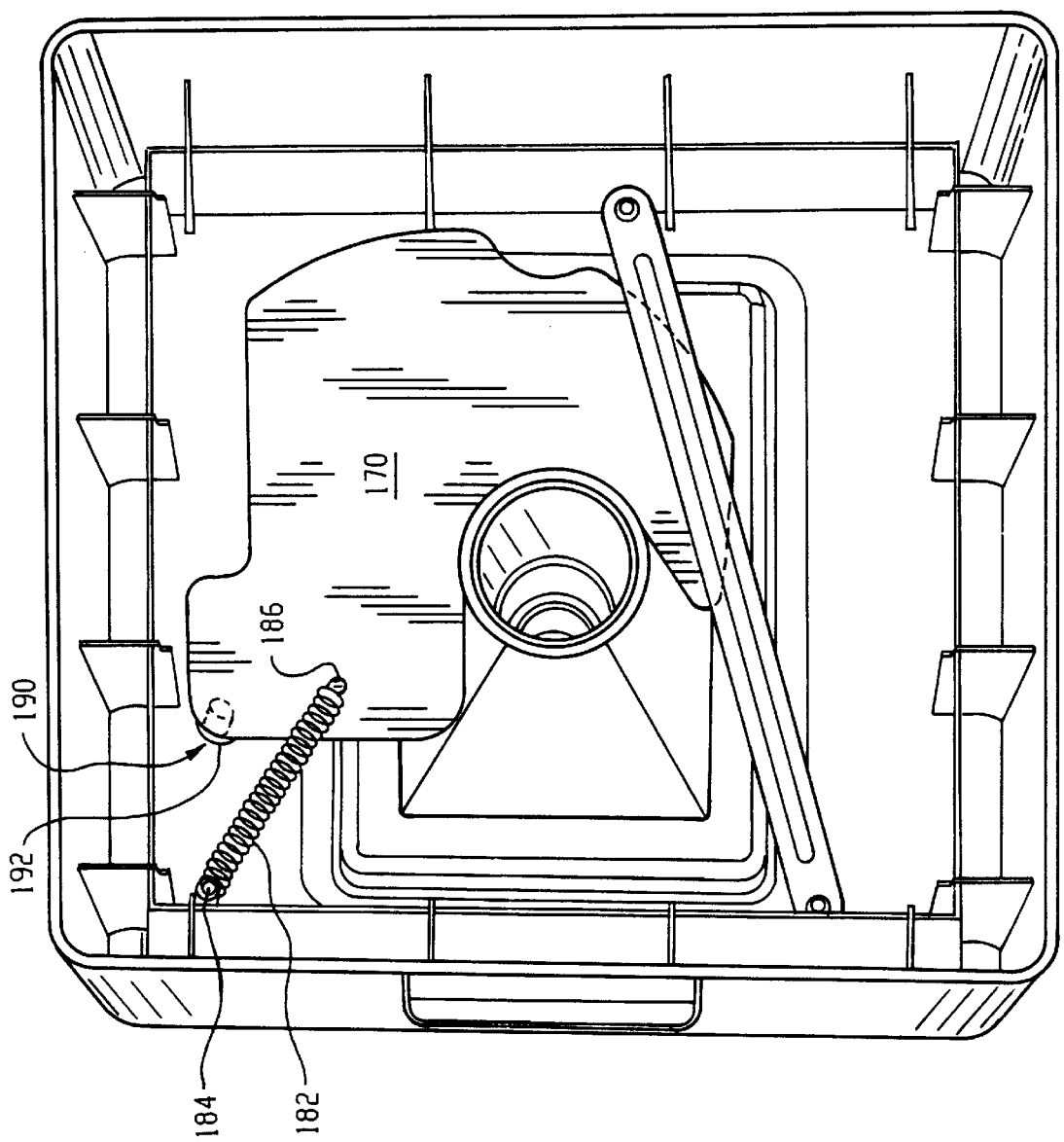
FIG. 6 is a rear isometric elevational view of the interface portion of the replaceable filter cartridge module taken along line 6—6 of FIG. 4 and illustrating the pre-filter housing and the door member in their respective intermated latched positions; and, FIGS. 7A–7C are front elevational views of the replaceable filter cartridge module with the pre-filter housing removed illustrating the opened, partially opened, and closed positions of the door member, respectively.

Preferably, the pivot door 170 is held biased into a closed position using a retaining spring 182 as best shown in FIG. 6. As shown there, the retaining spring is held fixed relative to the filter cartridge module 14 on a holding stud 184 and, similarly, is held fixed relative to the pivot door on the other end by a holding tab 186.

Figure 7A:
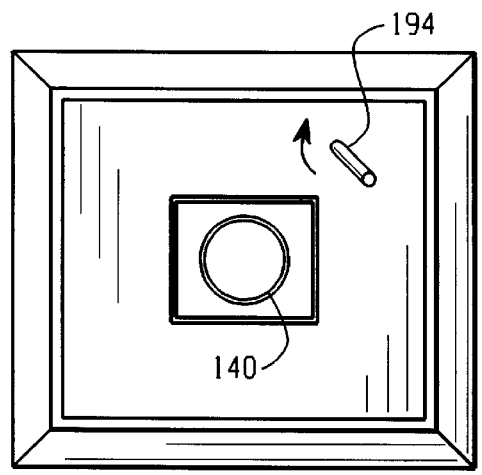

The holding stud is shown as a separate component but could be formed from a strip of the pivot door plate material that is stamped out and then bent into a suitable orientation. Preferably, the door is pivotable about an elongate pivot stud 190 formed integrally with the door and extending through a pivot bearing hole 192 formed through the input end 142 of the filter cartridge module 14. As shown best in FIGS. 7A–7C, the pivot stud 190 is connected on the input end with a manual lever 194. In FIG. 7A, the pivot door 170 is shown in its closed position whereat the input opening 140 in the filter cartridge module 14 is completely blocked off.

Figure 7B:
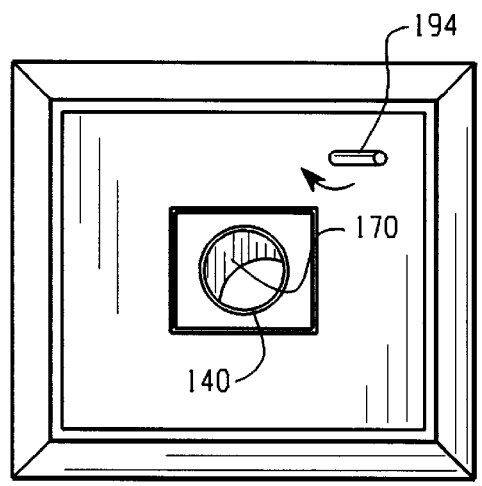

In accordance with the present invention, the manual lever 194 is rotated in the clockwise direction as shown in FIG. 7B to urge the pivot door 170 into rotation against the force of the retaining spring 182. As shown in FIG. 7B, the pivot door 170 is held in a partially opened position.

Figure 7C:
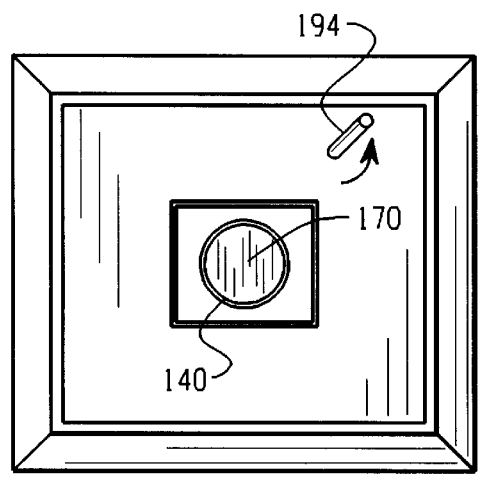

In FIG. 7C, the pivot door is rotated completely out of alignment with the input opening 140 to enable the annular grooved nose portion 156 of the pre-filter housing 120 to be inserted therein. In accordance with the present invention, an operator merely needs to rotate the manual lever 194 in a clockwise position until the pivot door 170 is moved out of the input opening 140. At that time, the pre-filter housing 120 can be inserted into the pocket region 174 formed in the input end 140 of the filter cartridge module. At that time, after the pre-filter housing is received into the pocket region, the manual lever 194 is released to enable the curved engagement edge 180 of the pivot door 170 to lockingly engage with the retaining groove 158 between the pair of circular shoulders 160, 162. The pre-filter housing is thus snugly held in place relative to the filter cartridge module.

The invention has been described with reference to the preferred embodiment. Obviously, modifications and alterations will occur to others upon a reading and understanding of this specification. As an example, the system could be equivalently configured so that the air exiting the system is routed directly to the exterior of the building. Also, vacuum motor current could be used to determine usable filter life based on the algorithm described as an alternative to actual or commanded motor speed or volume control switch position. The input switches and knobs could be replaced with radio frequency transmitter/receiver devices. It is intended to include all such modifications and alterations insofar as they come within the scope of the appended claims or the equivalents thereof.

Having thus described the invention, it is claimed:

1. An evacuation system for removing smoke generated during a medical procedure performed in an associated medical room, the evacuation system comprising:
    a replaceable filter cartridge module disposed in the associated medical room to permit replacement of a used filter cartridge module with a new filter cartridge module by personnel within the medical room, the filter cartridge module holding at least one filter and having an input opening on an input end adapted for selective connection with a pre-filter assembly and an exhaust opening, the filter cartridge module defining an internal passageway for communicating an airflow from the input opening to the exhaust opening through the at least one filter;
    a vacuum generator disposed outside of the associated medical room, the vacuum generator including a vacuum source and an elongate tube for establishing fluid communication between the exhaust opening of the filter cartridge module and the vacuum source, the vacuum source selectively generating said airflow through the tube and said internal passageway; and,
    the pre-filter assembly including a pre-filter housing and an elongate flexible suction hose member having a distal free end adapted for manipulation into position adjacent the medical procedure and a proximal end connected with the pre-filter housing, the pre-filter housing having an enlarged central region shaped to reduce the speed of said airflow to allow fluids entrained in the flow of air passing through the pre-filter housing to precipitate from the airflow and become trapped in the housing.

2. The evacuation system according to claim 1 wherein the pre-filter assembly includes a pre-filter medium held within said pre-filter housing, the pre-filter medium having a relatively coarse matt for trapping solid particles within the pre-filter housing while permitting smoke to pass therethrough.

3. The evacuation system according to claim 1 wherein the pre-filter housing includes a transparent viewing window to permit the pre-filter medium to be viewed without opening the pre-filter housing.

4. The evacuation system according to claim 1 wherein:
    the replaceable filter cartridge module holds at least one ultra low penetration air filter and at least one carbon filter; and,
    said internal passageway is adapted to communicate said airflow from the input opening to the exhaust opening through the at least one ultra low penetration air filter and through the at least one carbon filter.

5. An evacuation system for removing smoke generated during a medical procedure performed in an associated medical room, the evacuation system comprising:
    a pre-filter assembly including a pre-filter housing and an elongate flexible suction hose member having a distal free end adapted for manipulation into position adjacent the medical procedure and a proximal end connected with the pre-filter housing;
    a replaceable filter cartridge module disposed in the associated medical room to permit replacement of a used filter cartridge module with a new filter cartridge module by personnel within the medical room, the filter cartridge module holding at least one filter and having an input opening on an input end adapted for selective connection with the pre-filter assembly and an exhaust opening, the filter cartridge module defining an internal passageway for communicating an airflow from the input opening to the exhaust opening through the at least one filter;
    a vacuum generator disposed outside of the associated medical room, the vacuum generator including a vacuum source and an elongate tube for establishing fluid communication between the exhaust opening of the filter cartridge module and the vacuum source, the vacuum source selectively generating said airflow through the tube, said internal passageway and the pre-filter assembly to remove smoke from the medical procedure, the vacuum source being adapted to operate over a range of pump speeds to generate a corresponding range of flow rates of said airflow; and,
    a control unit having at least one manually operable mode control switch disposed in the associated medical room to permit access to the mode control switch by personnel within the medical room, the control unit being in operative control of said vacuum pump to selectively cause the vacuum pump to generate said airflow through said elongate tube, said internal passageway of the filter cartridge module, and said pre-filter assembly to remove smoke from the medical procedure based on a position of the manually operable mode control switch, said control unit further including an accumulated filter usage circuit for calculating a quantity of filter capacity available in said at least one filter based on a linear relationship between a filter usage time and said range of flow rates of said airflow.

6. The evacuation system according to claim 5 wherein:
    said accumulated filter usage circuit is adapted to generate a filter loading signal based on said calculated quantity of filter capacity available in said at least one filter; and,
    said control unit includes filter loading display device disposed in the associated medical room to provide visual indicia of said quantity of filter capacity available in said at least one filter to personnel within the associated medical room.

7. The evacuation system according to claim 6 wherein the accumulated filter usage circuit is adapted to determine said quantity of filter capacity available in said at least one filter by adjusting a frequency of a usage counter in proportion to at least a one of i) said range of flow rates and ii) said position of the manually operable volume control switch.

8. The evacuation system according to claim 7 further including means for resetting said usage counter when said used filter cartridge module is replaced with said new filter cartridge module by personnel in the medical room.

9. The evacuation according to claim 8 wherein the means for resetting the usage counter includes a switch operatively connected to the control unit and held in the medical room in a fixed position relative to said replaceable filter cartridge module for generating a signal when said used filter cartridge module is replaced with said new filter cartridge module.

10. The evacuation according to claim 5 further including a footswitch operatively connected with the control unit for selectively generating a command signal when activated by personnel within the medical room, the command signal being used by the control unit to selectively cause the vacuum source to generate said airflow.

11. The evacuation system according to claim 10 wherein:
the manually operable mode control switch is selectively positionable in a first position, a second position, and a third position; and,
the control unit is in operative control of said vacuum pump to i) selectively generate said airflow when the mode control switch is in said first position, ii) selectively terminate said airflow when the mode control switch is in said second position, and iii) selectively generate said airflow when said command signal is generated by the footswitch and the mode control switch is in said third position.

12. An evacuation system for removing smoke generated during a medical procedure performed in an associated medical room, the evacuation system comprising:
a pre-filter assembly including a pre-filter housing and an elongate flexible suction hose member having a distal free end adapted for manipulation into position adjacent the medical procedure and a proximal end connected with the pre-filter housing;
a replaceable filter cartridge module disposed in the associated medical room to permit replacement of a used filter cartridge module with a new filter cartridge module by personnel within the medical room, the filter cartridge module holding at least one filter and having an input opening on an input end adapted for selective connection with the pre-filter assembly and an exhaust opening, the filter cartridge module defining an internal passageway for communicating an airflow from the input opening to the exhaust opening through the at least one filter; and,
a vacuum generator disposed outside of the associated medical room, the vacuum generator including a vacuum source and an elongate tube for establishing fluid communication between the exhaust opening of the filter cartridge module and the vacuum source, the vacuum source selectively generating said airflow through the tube, said internal passageway and the pre-filter assembly to remove smoke from the medical procedure, said input end of the filter cartridge module including a first mechanical connection surface adapted for selective connection with the pre-filter assembly and the pre-filter assembly including a second mechanical connection surface formed on the pre-filter housing and shaped oppositely from the first mechanical connection surface to permit the filter cartridge module and the pre-filter assembly to be selectively intermatably engaged at the first and second connection surfaces.

13. The evacuation system according to claim 12 wherein:
the filter cartridge module includes a shutter-type pivot door member selectively movable between a first closed position to block said input opening and a second opened position to permit substantially unrestricted access to said input opening; and,
the pre-filter assembly includes an annular grooved nose portion with a retaining groove adapted to receive a lead edge portion of the shutter-type pivot door member to permit selective connection between the filter cartridge and the pre-filter assembly.

14. The evacuation system according to claim 12 in combination with a medical equipment support apparatus.

15. The evacuation system according to claim 14 wherein the evacuation system is integrated into said medical equipment support apparatus.

16. A surgical smoke evacuation system for removing smoke generated during a medical procedure in an associated medical room using a vacuum generator including an elongate tube and a vacuum source selectively generating a selectively variable airflow rate through the tube, the surgical smoke evacuation system comprising:
a pre-filter assembly including a pre-filter housing and an elongate flexible suction hose member having a distal end adapted for manipulation into position adjacent the medical procedure and a proximal end connected with the pre-filter housing, pre-filter housing including a first mechanical connection area; and,
a replaceable filter cartridge module to permit replacement of a used filter cartridge module with a new filter cartridge module, the filter cartridge module holding at least one filter and having an input opening on an input end adapted for selective connection with the pre-filter assembly and an exhaust opening connected to said elongate tube, the filter cartridge module defining an internal passageway for communicating an airflow from the input opening to the exhaust opening through the at least one filter, the input end of the filter cartridge module including a second mechanical connection area shaped oppositely from the first mechanical connection area to permit the filter cartridge module and the pre-filter assembly to be selectively intermatably engaged at the first and second connection areas, the second mechanical connection area of the filter cartridge module including a shutter-type pivot door member selectively movable between a first position to block said input opening and a second position to permit substantially unrestricted access to said input opening and the first mechanical connection area of the pre-filter assembly including an annular grooved nose portion with a retaining groove adapted to receive a lead edge portion of the shutter-type pivot door member to permit said selective intermatable engagement between the filter cartridge and the pre-filter assembly.

17. The surgical smoke evacuation system according to claim 16 further including a control unit adapted to calculate a quantity of filter capacity available in said at least one filter based on said variable airflow rate.

18. The surgical smoke evacuation system according to claim 17 wherein said control unit is adapted to generate a filter loading signal based on said quantity of filter capacity available in said at least one filter calculated and includes a filter loading display device to provide visual indicia of said quantity of filter capacity available in said at least one filter.

19. The surgical smoke evacuation system according to claim 18 wherein the control unit is adapted to determine said quantity of filter capacity available in said at least one filter by adjusting a frequency of a usage counter in proportion to said variable airflow rate.

20. The surgical smoke evacuation system according to claim 19 further including means for resetting said usage counter when said used filter cartridge module is replaced with said new filter cartridge module.

21. The surgical smoke evacuation system according to claim 20 wherein the means for resetting the usage counter includes a switch operatively connected to the control unit and held in a fixed position relative to said replaceable filter cartridge module for generating a signal when said used filter cartridge module is replaced with said new filter cartridge module.

* * * * *

UNITED STATES PATENT AND TRADEMARK OFFICE
CERTIFICATE OF CORRECTION

PATENT NO. : 6,203,590 B1
DATED : March 20, 2001
INVENTOR(S) : Byrd et al.

It is certified that error appears in the above-identified patent and that said Letters Patent is hereby corrected as shown below:

<u>Title page,</u>
Please insert the following Assignee information: -- (73) Assignee: Steris Corporation, Mentor, OH (US) --

Signed and Sealed this

Twenty-eighth Day of August, 2001

*Attest:*

*Attesting Officer*

NICHOLAS P. GODICI
*Acting Director of the United States Patent and Trademark Office*